(12) United States Patent
Avots

(10) Patent No.: US 10,912,900 B2
(45) Date of Patent: Feb. 9, 2021

(54) SYSTEM AND METHOD FOR VAPORIZING SUBSTANCES FOR INHALATION

(71) Applicant: Sean Avots, Bothell, WA (US)

(72) Inventor: Sean Avots, Bothell, WA (US)

( * ) Notice: Subject to any disclaimer, the term of this patent is extended or adjusted under 35 U.S.C. 154(b) by 393 days.

(21) Appl. No.: 15/934,912

(22) Filed: Mar. 23, 2018

(65) Prior Publication Data
US 2018/0272083 A1 Sep. 27, 2018

Related U.S. Application Data

(60) Provisional application No. 62/475,806, filed on Mar. 23, 2017.

(51) Int. Cl.
*A61M 11/00* (2006.01)
*A61M 11/04* (2006.01)
(Continued)

(52) U.S. Cl.
CPC ......... *A61M 11/048* (2014.02); *A24F 47/006* (2013.01); *A24F 47/008* (2013.01); *A61M 15/0001* (2014.02); *A61M 15/0065* (2013.01); *A61M 15/06* (2013.01); *A24F 47/004* (2013.01); *A61M 16/1075* (2013.01);
(Continued)

(58) Field of Classification Search
CPC ........ A24F 13/00; A24F 13/14; A24F 47/002; A24F 47/006; A24F 47/008; A61B 2562/0295; A61B 5/14532; A61B 5/150022; A61B 5/150167; A61B 5/150175; A61B 5/150358; A61B 5/150412; A61B 5/150519; A61B 5/150748; A61B 5/15113; A61B 5/15117; A61B 5/15153; A61B 5/15163; A61B 5/157; A61B 5/4839; A61M 11/041; A61M 11/042; A61M 15/06; A61M 16/107; A61M 16/1075; A61M 2005/3103; A61M 5/1723; A62B 9/003; G01N 33/48785
See application file for complete search history.

(56) References Cited

U.S. PATENT DOCUMENTS 4,019,511 A * 4/1977 Choporis ............... A62B 9/003
128/203.26
4,036,224 A * 7/1977 Choporis .............. A61M 15/06
128/202.21
(Continued)

*Primary Examiner* — Annette Dixon
(74) *Attorney, Agent, or Firm* — Christopher Mayle; Thomas E. LaGrandeur; Bold IP, PLLC

(57) ABSTRACT

Embodiments are directed to a portable vaporization device whereby the vaporization device extracts active compounds from various liquids, fluids, oils, and waxes for inhalation and may heat up any desired amount of a vaporizable substance. The vaporization device has a button that ignites the liquefied gas to produce a flame. The vaporization device has a button to start the feeding mechanism, which pushes the vaporizable substance against a tube that the flame is heating to turn the vaporizable substance more viscous where it then runs down the tube into a series of wires, further heating the vaporizable substance, turning the vaporizable substance into vapor. The dosage of the vaporization device may be set to provide a lower amount of vapor to a greater amount of vapor. The button may be pushed to produce as much vapor as desired.

20 Claims, 9 Drawing Sheets

(51) Int. Cl.
*A61M 15/00* (2006.01)
*A24F 47/00* (2020.01)
*A61M 15/06* (2006.01)
*A61M 16/10* (2006.01)

(52) U.S. Cl.
CPC ............... *A61M 2205/3368* (2013.01); *A61M 2205/502* (2013.01); *A61M 2205/581* (2013.01); *A61M 2205/583* (2013.01)

(56) References Cited

U.S. PATENT DOCUMENTS

| | | | | |
|---|---|---|---|---|
| 5,472,001 | A * | 12/1995 | Nicholson | A24F 13/00 131/185 |
| 5,553,607 | A * | 9/1996 | Chiu | A61M 11/041 128/203.26 |
| 6,164,287 | A * | 12/2000 | White | A24F 47/008 131/194 |
| 9,974,333 | B1 * | 5/2018 | Disner | A24F 47/002 |
| 2011/0282173 | A1 * | 11/2011 | Fonduca | A61B 5/150748 600/365 |
| 2013/0014755 | A1 * | 1/2013 | Kumar | A24F 47/006 128/202.21 |
| 2013/0228170 | A1 * | 9/2013 | Alper | A24F 47/006 128/202.21 |

* cited by examiner

SYSTEM AND METHOD FOR VAPORIZING SUBSTANCES FOR INHALATION

CROSS REFERENCE TO RELATED APPLICATION

This application claims priority to a prior-filed provisional Application Ser. No. 62/475,806 filed on Mar. 23, 2017.

FIELD OF DISCLOSURE

The overall field of this invention is a system and method for vaporizing vaporizable substances. More specifically, the field of the invention is a self-contained vaporization device for vaporizing vaporizable substances to produce a vapor for inhalation for quick absorption into the bloodstream.

BACKGROUND

Vaporizers provide an alternative to smoking that avoids the inhalation of various irritating toxic and carcinogenic compounds. Smoking has dangerous side effects on the body, which diminishes overall health and can lead to cancer occurring in various organs such as the lungs, esophagus, larynx, mouth, throat, kidney, bladder, pancreas, stomach, and cervix. Cigarettes also generate sidestream smoke, which is smoke that moves into the surrounding air, leading to "secondhand" smoke to bystanders, which can be just as deadly as the smoke inhaled directly into the user's lungs. Vaporization avoids these complications by applying liquids made up only of ingredients such as water, nicotine, flavoring, and a VG (vegetable glycerin)/PG (propylene glycol) mixture and only heating the liquid to a temperature where combustion does not occur for the dangerous toxins and constituents. Vaporizing at a specific temperature also has the added benefit of not destroying the active compounds because of the excess heat from smoking, which improves both potency and flavor.

Vaporizers are now more popular than ever with various designs and types now available on the market but still have many limitations. Electronic vaporizers have significant restraints including requiring a substantial amount of power to heat the substances to the necessary temperature to produce a vapor. This leads to extensive recharging times that require the user to wait before operating or having to rely on disposable batteries that need to be replaced at inconvenient times and should be properly disposed of to prevent harming of the environment.

Most common gas-powered vaporizers require the user to place the vaporizable substances in the vaporization chamber before heating the device. Any vaporizable substances placed in the device will be heated and cannot be set-aside for later use. The user also has to remove the vaporizable substances every time from a separate container, such as pouch or bag, and place the substance carefully in the device piece-by-piece instead of being able to inhale a metered dose selected by the user in the device itself. These shortcomings in gas-powered vaporizers lead to a strain on the portability factor of the vaporizers, forcing the user to carry around multiple apparatuses.

Other vaporizers are able deliver a metered dose for the user to inhale. On each cartridge are multiple sections containing a predetermined amount of vaporizable substance as well as a heating element. When the drug dose cartridge is loaded into the vaporizer, a mechanical lever pulls out a section to be heated when in contact with an electric heating element to vaporize the constituent, which the user can then inhale. However, the amount of vaporizable substance is predetermined before loading the vaporizer, thus the user is not able to change the desired amount to be inhaled spontaneously. Another setback is that each cartridge has to be specially made, needing extra elements such as a heating coil to be heated in each section. Accordingly, there is still a great need for a system and apparatus and method for improved vaporization that overcomes the many shortcomings of conventional devices.

SUMMARY

It is an object of the present description to provide a vaporization device for vaporizing substances, including: a housing having a storage compartment; a vaporizable substance stored within the storage compartment; a flame generator having a tube, the tube including a conductive-based heating surface; and a feeding mechanism configured to place the vaporizable substance from the storage compartment into contact with the tube, the feeding mechanism including a button, a spring, and a pusher, the button and pusher are engageable, the button and pusher having a first position when disengaged and a second position when engaged, the button coupled to the storage compartment whereby when the button is engaged an amount of the vaporizable substance is moved out of an opening of the storage compartment, the spring configured to be actuable on the pusher to apply force on the pusher, the pusher in the first position dimensioned to cover the opening of the storage compartment, the button in the first position configured to prevent force of the spring on the pusher, the button in the second position configured to no longer prevent force of the spring on the pusher, the pusher in the second position dimensioned to not cover the opening of the storage compartment.

It is an object of the present description to provide a method of inhaling a vaporizable substance from a vaporizer, the vaporizer including a housing having a storage compartment for storing vaporizable substances, a flame generator, a tube accommodating the flame generator, one or more wires connected to the tube, and a feeding mechanism; engaging the flame generator causing the tube to be heated by a flame; engaging the feeding mechanism causing an amount of vaporizable substance from the storage compartment to come into contact with the tube, the vaporizable substance becoming less viscous and coming into contact with the wires to produce a vapor; and inhaling the vapor, adjusting a dial, the dial changing the amount of released vaporizable substance from the storage compartment when the feeding mechanism is engaged.

It is an object of the present description a portable vaporization device for vaporizing substances, including: a housing having a storage compartment; vaporizable substance stored within the storage compartment; a flame generator; a tube accommodating the flame generator, the tube a conductive-based heating element, one or more wires connected to the tube; a feeding mechanism configured to place the vaporizable substance from the storage compartment into contact with the tube and the wires; an air inlet having a first end and a second end, the first end connected to the housing; an outlet having a first end and a second end, the first end connected to the housing, the second connected to a balloon, the air outlet and air inlet configured whereby when air is moved through the air inlet, vapor is forced through the outlet, filling the balloon.

BRIEF DESCRIPTION OF DRAWINGS

The present invention will be described by way of exemplary embodiments, but not limitations, illustrated in the accompanying drawings in which like references denote similar elements, and in which.

DETAILED DESCRIPTION

Figure 1:
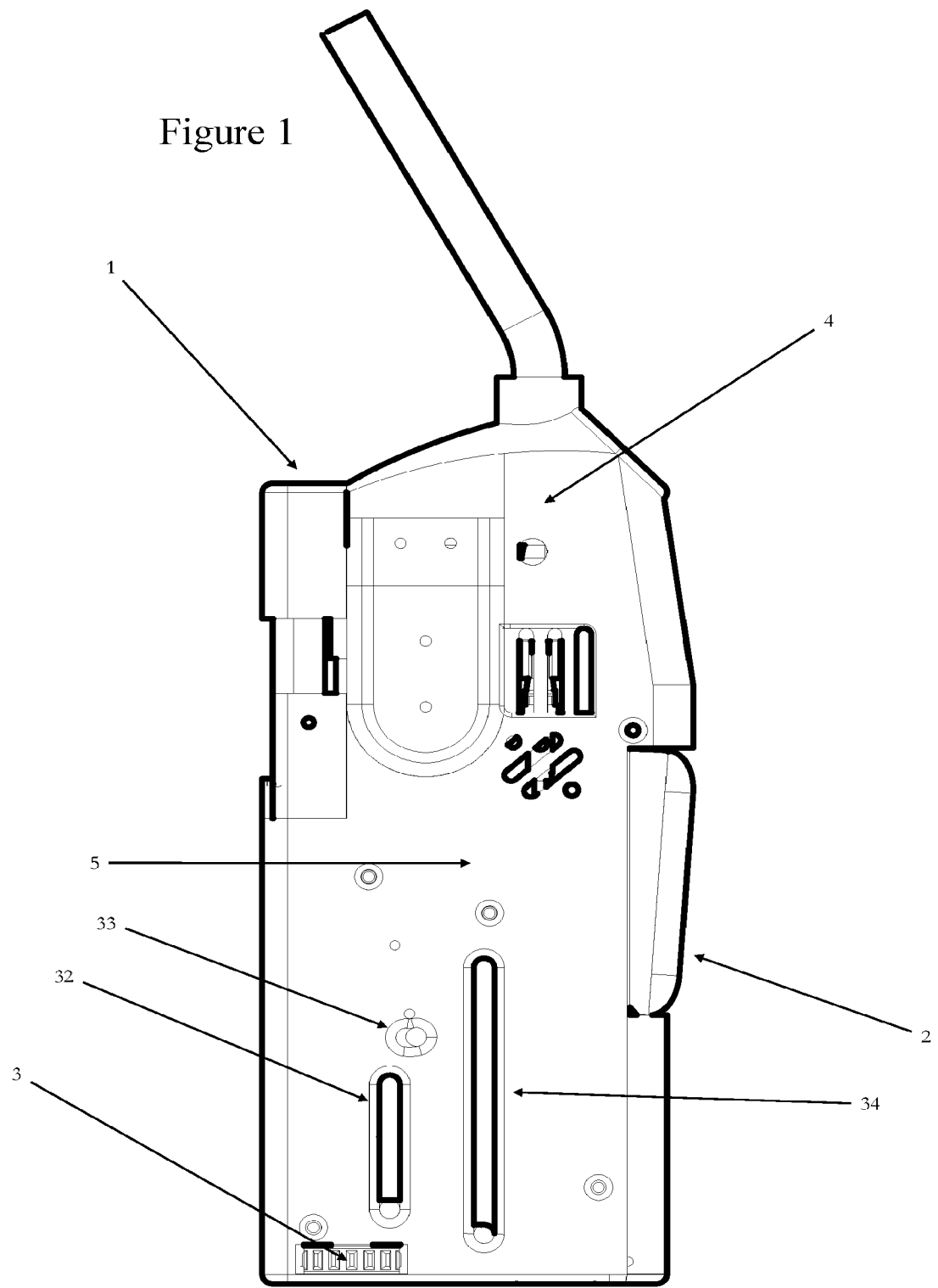
FIG. 1 shows a side view of an assembled vaporization device with the upper housing component attached to the lower housing component in accordance with an illustrative embodiment.

In the Summary above and in this Detailed Description, and the claims below, and in the accompanying drawings, reference is made to particular features of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

"Exemplary" is used herein to mean "serving as an example, instance, or illustration." Any aspect described in this document as "exemplary" is not necessarily to be construed as preferred or advantageous over other aspects Throughout the drawings, like reference characters are used to designate like elements. As used herein, the term "coupled" or "coupling" may indicate a connection. The connection may be a direct or an indirect connection between one or more items. Further, the term "set" as used herein may denote one or more of any item, so a "set of items," may indicate the presence of only one item, or may indicate more items. Thus, the term "set" may be equivalent to "one or more" as used herein.

In the following detailed description, numerous specific details are set forth in order to provide a more thorough understanding of the one or more embodiments described herein. However, it will be apparent to one of ordinary skill in the art that the invention may be practiced without these specific details. In other instances, well-known features have not been described in detail to avoid unnecessarily complicating the description.

The present disclosure recognizes the unsolved need for a gas powered portable vaporization device and its method of use that is able to extract active compounds from various liquids, fluids, oils, and waxes for inhalation whereby the user may heat up any desired amount of vaporizable substance that the user wishes using a feeding mechanism within the vaporization device. This provides a more personalized, entertaining, and interactive vaporizing experience where the user may heat up any desired amount of vaporizable substance that the user wishes. If the user wants to inhale a larger amount of vapor, then the user can set the vaporization device to dispense a greater dosage. If the user wants to inhale fewer vapors, then the user can set the vaporization to dispense a smaller dosage. The user may also dispense as many dosages as they wish.

Figure 2:
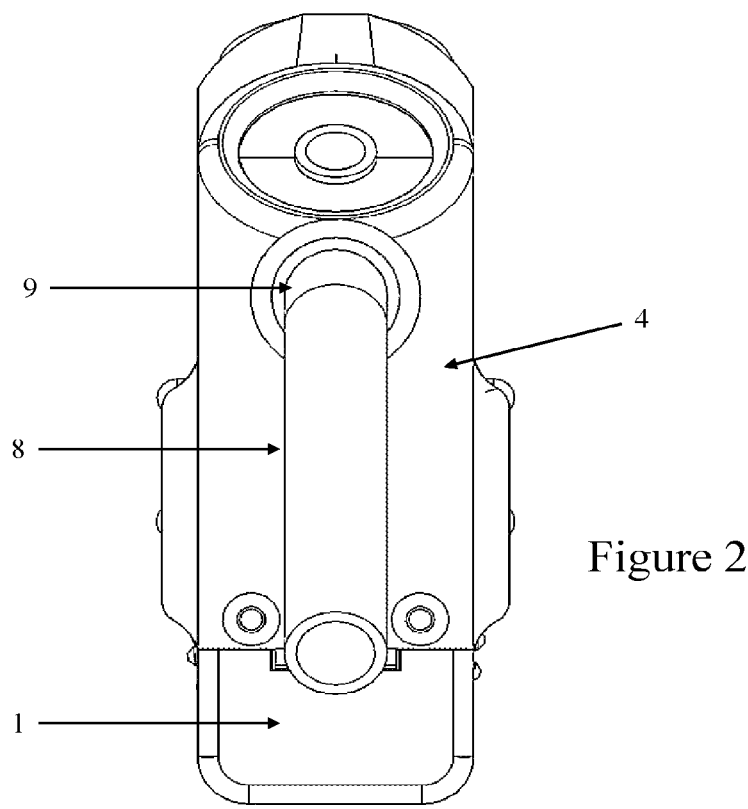
FIG. 2 shows a top view of the assembled vaporization device shown in FIG. 1 in accordance with an illustrative embodiment.
Figure 3:
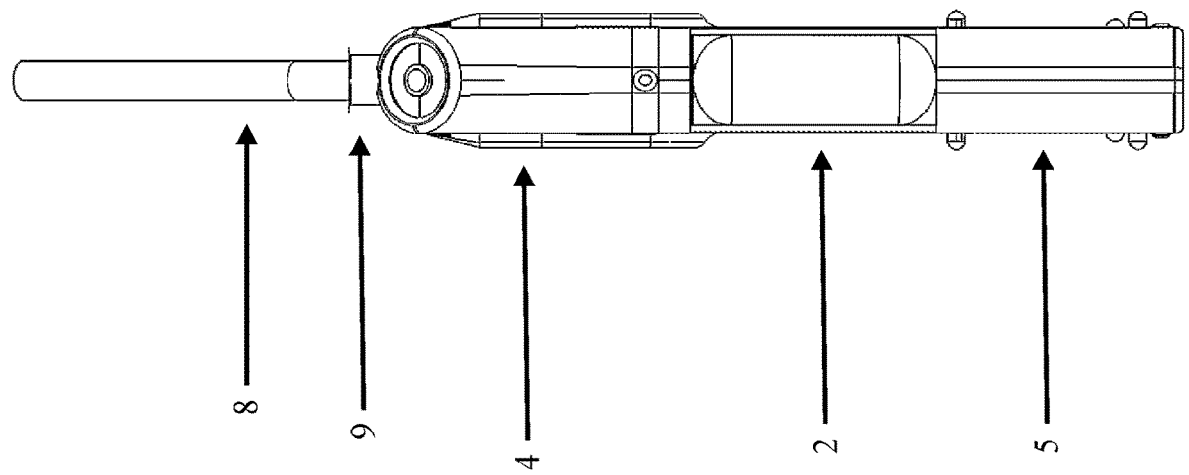
FIG. 3 shows a front view of the assembled vaporization device shown in FIG. 1 in accordance with an illustrative embodiment.
Figure 4:
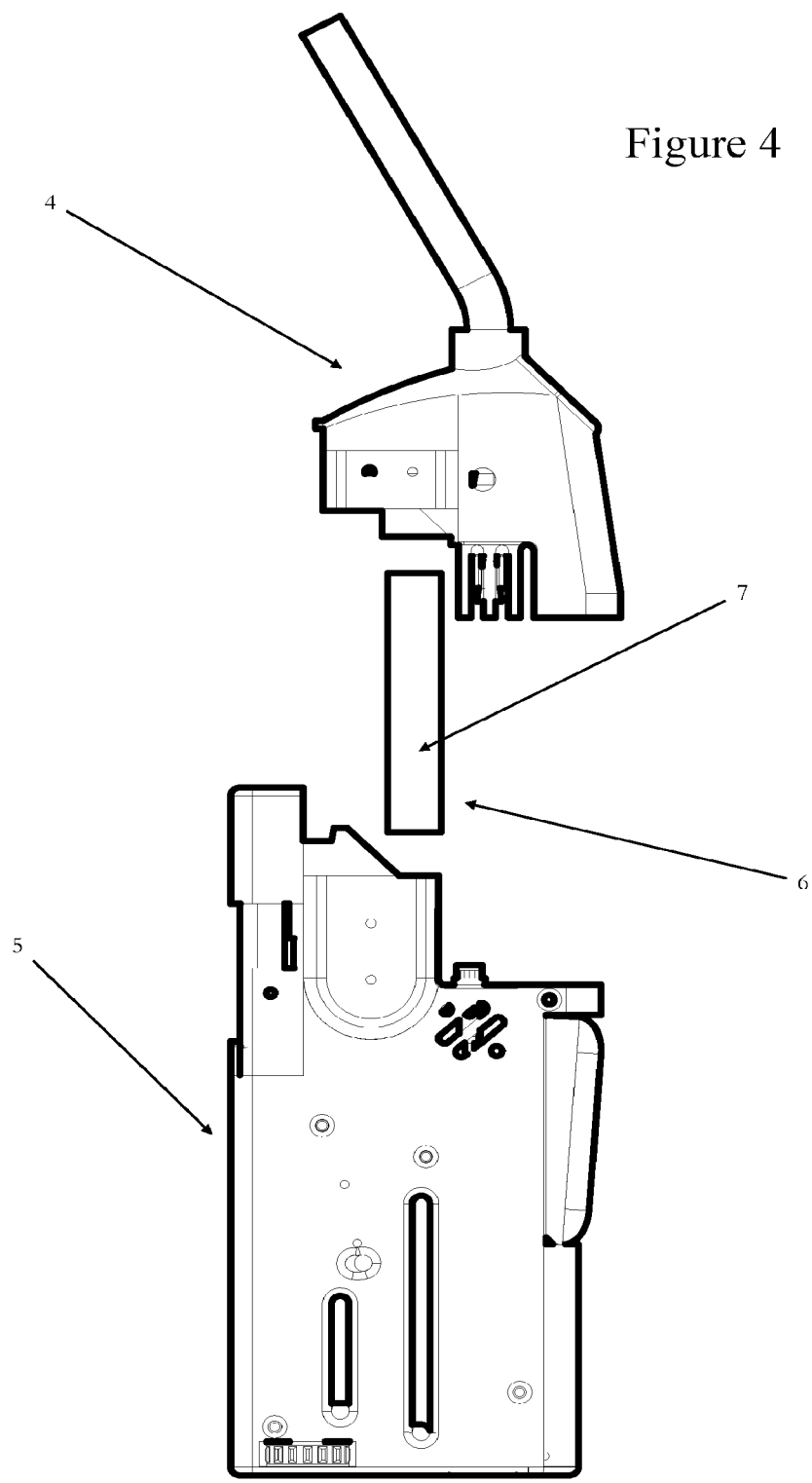
FIG. 4 shows a side view of the separate housing components and the cartridge that loads into a vaporization device in accordance with an illustrative embodiment.

Turning to FIG. 1, FIG. 1 shows a side view of an assembled vaporization device, according to one embodiment, with the upper housing component attached to the lower housing component. A vaporization device, as depicted in the exemplary embodiment shown in FIG. 1, may include, in one or more embodiments two parts. In one embodiment, a vaporization device, as shown in FIG. 1, may include an upper housing component such as upper housing component 4 and a lower housing component such as lower housing component 5, which may serve as casing element for the inner mechanisms of the vaporization device. FIG. 2 (which shows a top view of the vaporization device in FIG. 1) shows the separated housing components 4 and 5 and a cartridge such as cartridge 6 for holding a vaporizable substance such as vaporizable substance 7 such as oils, liquid, hydrocarbons, waxes, e-liquids, extracts, other substances as well as any combination of these substances.

In one non-limiting embodiment, the housing is preferably made of plastic, although other materials such as aluminum, stainless steel, or other metals and composites may also be used without limitation, which are suitable for the vaporization of substances without becoming distorted or burnt.

Upper housing component 4 and lower housing component 5 may be connected together by a draw latch with a strike (not shown in Figures) on lower housing component 5 and a base, handle, and draw hook located on the upper housing component 4 whereby the draw hook is moved under the strike and the handle is pulled down thereby locking housing components 4 and 5 together. To separate housing components 4 and 5, in one or more embodiments, the handle is pulled up and the draw hook may be removed from under the strike. In further non-limiting embodiments, the base, handle, and draw hook may be located on the lower housing component 5 while draw latch with a strike is on the upper housing component 4.

In other non-limiting embodiments, one housing component (e.g. upper housing component 4) has protrusions and the other housing component (e.g. lower housing component 5) may have engagement holds whereby the protrusions slide into the engagement holds. To separate components 4 and 5, a switch, button, or activation apparatus may be pressed to retract the protrusions so the component may be removed from the other component. In further non-limiting embodiments, the housing may be a single continuous component rather than two separately distinct housing components whereby the mechanisms of the vaporization device are enclosed in the single housing.

Figure 5:
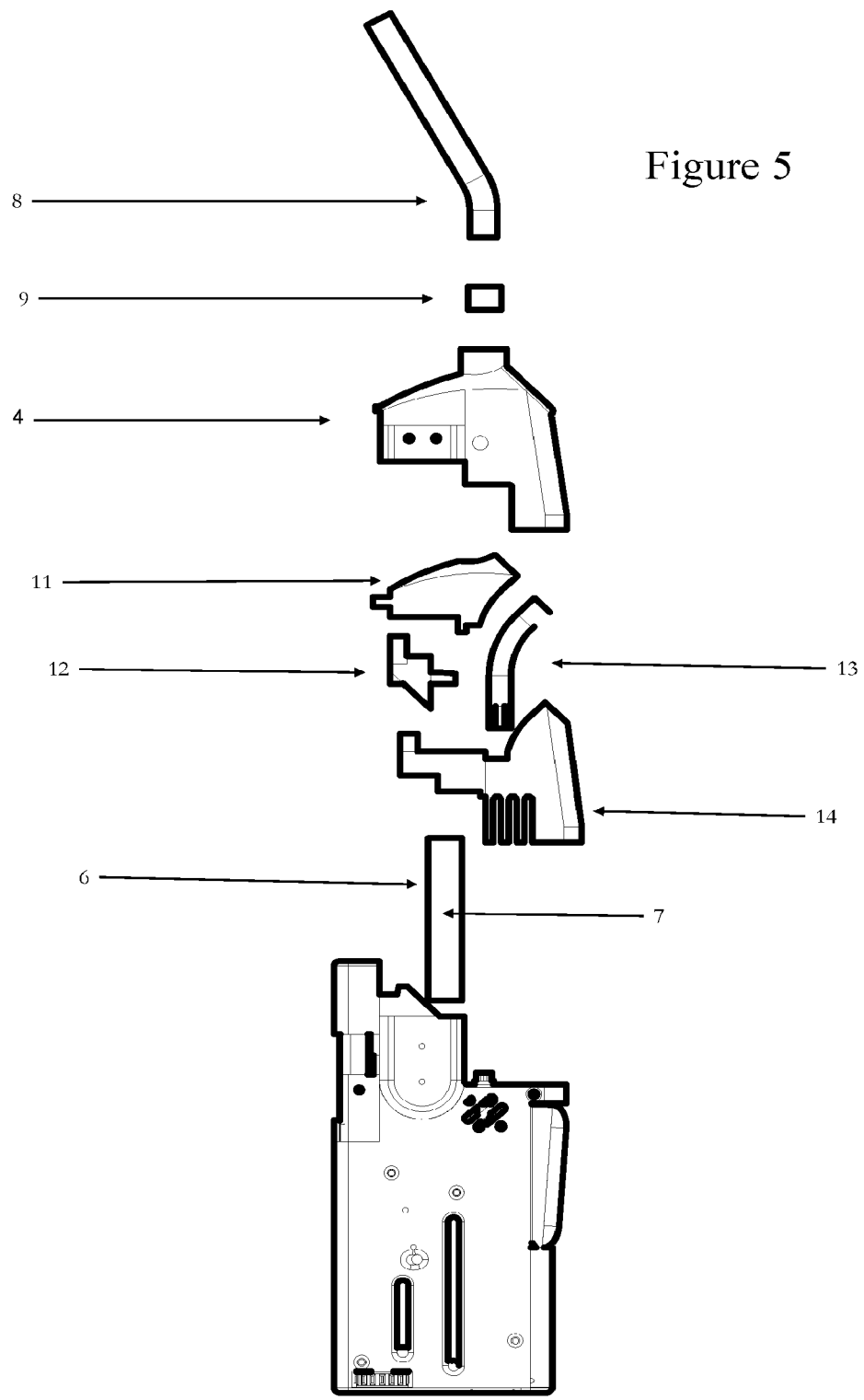
FIG. 5 shows an exploded view of the upper housing component of the vaporization device of FIG. 1 in accordance with an illustrative embodiment.
Figure 6:
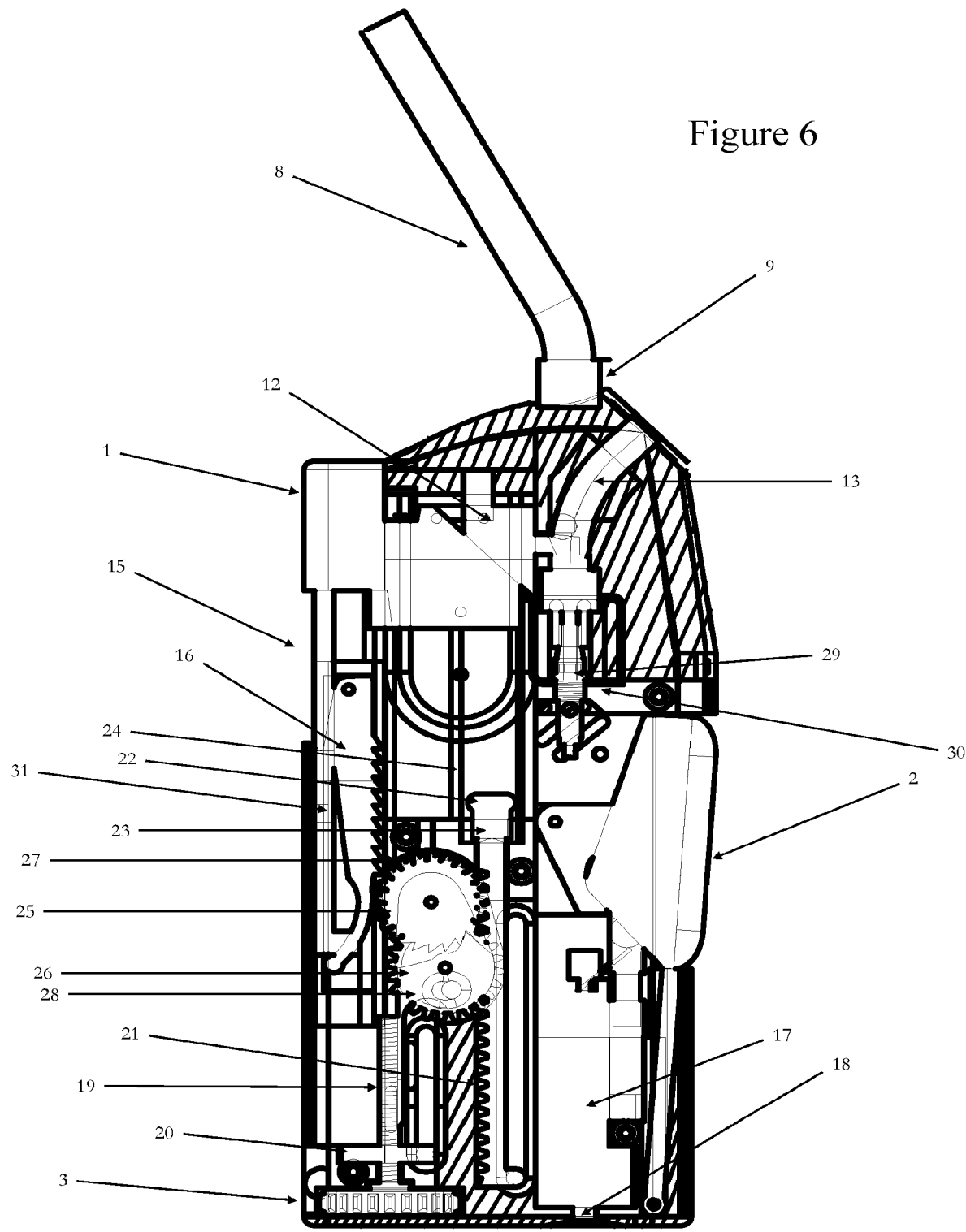
FIG. 6 shows a cross section view of internal mechanisms of the vaporization device in accordance with an illustrative embodiment.

FIG. 6 shows an interior view of some of the interior components to activate the feeding mechanism of the vaporization device to push vaporizable substance 7 from cartridge 6 and into flame tube assembly 13 to be heated, of the exemplary vaporization device discussed above with respect to FIGS. 1-5. Lower housing component 5 may include a button such as button 1 extruding from lower housing component 5. Button 1 may be a button (including any type of button known in the art) but in some embodiments is hollow with an interior mounted to a slide such as slide 15 where slide 15 and button 1 project through an opening in lower housing component 5. Slide 15 may be slidably mounted to lower housing component 5. Slide 15 may be moved up and down in conjunction with button 1 when engaged by a user. Slide 15 may be connected to a bus such as bus 31. Bus 31 may be connected to a rack such as rack 16 (as shown in FIG. 6).

In one embodiment, to activate the feeding mechanism of the vaporization device to push vaporizable substance 7 from cartridge 6 and into a flame tube assembly such as flame tube assembly 13, a user may depress button 1, thus causing button 1, slide 15, rack 16, and bus 31 move axially in a linear motion in a downward direction until bus 31 comes into contact with the inside of the bottom of part of the lower housing component 5. A first compression spring (not shown) attached to a horizontal platform connected to lower housing component 5 and the bottom side of button 1 may be provided for resiliently urging button 1, slide 15, rack 16, and bus 31 axially in the linear direction in an upward direction enabling button 1 to be reset to button 1's original position where it then may be depressed once again by the user. In some embodiments the feeding mechanism may have one or spring device or other apparatuses for preventing the button 1 and slide 15 to fall out of lower housing component 5 or to stop button 1 and slide 15 from extending further than needed.

The rack 16 may engage with a gear train connected to inside of lower housing component 5 when button 1 is depressed by the user. The gear train may include one or more gears. As shown in FIG. 6, in one exemplary embodiment, it may be preferable to have three gears such as gears 25, 26, and 27, gear 27 positioned behind 25 on the front view, arranged as one or more gear trains whereby rack 16 engages the teeth on the first circular gear; causing first circular gear 25 to move relative to rack 16 thereby translating the linear motion of rack 16 into rotational motion of first circular gear 25. The gear train is aligned so that the rotational movement of first circular gear 25 is transferred in concert to a second circular gear 26 and then to a third circular gear 27. Third circular gear 27 engages the teeth of a straight rack such as straight rack 21 positioned in lower housing component 5; initiating straight rack 21 to move relative to third circular gear 27 translating the rotational motion of third circular gear 27 to the linear motion of straight rack 21.

A ratchet such as ratchet 28 may be connected to the gear train whereby ratchet 28 engages the teeth of one or more of gears 25, 26, and 27 to prevent axial movement of straight rack 21 in the downward direction. Straight rack 21 may have a nob, visible through an opening such as opening 34 (shown in FIG. 1) in lower housing component 5.

Ratchet 28 may have a toggle such as toggle 33 (also shown in FIG. 1), which is visible through the outside of lower housing component 5 whereby toggle 33 may stop or allow ratchet 28 to prevent movement of straight rack 21 in the downward direction. For instance when cartridge 6 is emptied of vaporizable substance 7, toggle 33 may be flipped or held back allowing the nob on straight rack 21 to be pushed down putting the straight rack into its original position and cartridge 6 may then be refilled and placed within the vaporization device or may be replaced with a new cartridge. Cartridge 6 may be any type of suitable cartridge known in the art and includes vaporizable substance 7. Cartridge may be sold in pre-filled disposable cartridges or refillable tanks whereby users refill the cartridge with vaporizable substance. Cartridges may also be made at home or used in a kit for consumers to make their own.

In some embodiments there may be an opening on the bottom of lower housing component 5 exposing a dosage dial such as dosage dial 3. Dosage dial 3, may be a threaded nut for adjusting the dosage of vaporizable substance 7 released from cartridge 6. Dosage dial 3 may be connected to a threaded rod such as threaded rod 19 arranged into the interior of dosage dial 3. Stop 20 may have interior threading and a hole larger than the circumference of threaded rod 19 and is connected to the exterior threading of the treaded rod whereby stop 20 moves in the axial direction e.g. up and down in response to the rotating motion of dosage dial 3. For example, a counter clockwise movement of threaded rod 19 moves stop 20 upwards in the axial direction. However, in other non-limiting embodiments a clockwise movement of threaded rod 19 moves stop 20 upwards in the axial direction.

Markings may be etched on the exterior of lower housing component 5's housing near opening 34 on lower housing component 5 where stop 20 may be visible through the exterior of lower housing component 5. The markings may show how large of a dosage will dispense when operating the vaporization device to provide information on the expected dosage to a user. Dosage dial 3, threaded rod 19, and stop 20 are positioned within lower housing component 5 whereby the downward axial movement of the button bus 31 is limited when the button 1 is depressed by the upward axial movement of the stop 20 thus decreasing the contact of button rack 16 with gears 25, 26, and 27.

As shown in FIG. 6, a refillable fuel reservoir such as refillable fuel reservoir 17 may be positioned inside lower housing component 5. Refillable fuel reservoir 17 may store liquefied gas which in the preferred embodiment is butane under vapor pressure in its liquid form. Nevertheless, this is a non-limiting embodiment and refillable fuel reservoir 17 may store any other fuel known by those of ordinary skill in the art such as, without limitation, charcoal lighter fluid or other hydrocarbons. A refill inlet valve such as refill inlet valve 18 is located at an outlet located on the bottom of fuel reservoir 17, appearing on the outside of lower housing component 5. Refill inlet valve 18 may be used to refill fuel into the fuel reservoir by refilling the liquefied gas through refill inlet valve 18. When in operation, the liquefied gas may evaporate into gas when a control valve located at an outlet of the fuel reservoir is opened. The gas is delivered to a burner such as burner 29 in lower housing component 5 from fuel reservoir 17 through the control valve and a fuel line, which is directed upward in the casing to the burner 29.

Air is then forced rapidly through openings into burner 29 by the Venturi effect. The Venturi effect is the reduction in fluid pressure that results when a fluid flows through a constricted section of pipe. In lower housing component 5, there may be a piezoelectric ignition mechanism (not shown. As known in the art, a piezoelectric igniter uses a phenomenon called piezo-electric effect to generate an electric spark, which ignites the combustible gas. The piezoelectric ignition mechanism includes a piezoelectric material, an electric wire, one or more metal bases, and a spring-loaded small hammer to forcefully strike the piezoelectric material to produce a spark or electric current. Typically when a button is pressed, a hammer is moved away from a piezoelectric crystal. A spring releases the hammer, which hits the piezoelectric crystal creating a spark.

The piezoelectric material is preferably made of quartz but any material that produces an electric current when the material is placed under mechanical stress may be suitable. Activating the piezoelectric ignition mechanism causes the hammer to strike the quartz. The striking action causes an electric charge to propagate through a wire upward to flame tube assembly such as flame tube assembly 13 creating a spark next to burner 29 igniting the air fuel mixture.

The lower housing component 5 may include a lever such as lever 2 extruding from lower housing component (e.g. as shown in FIG. 1). When lever 2 is depressed by a user, the control valve is opened, releasing the gas upwards through the fuel line and the piezoelectric ignition mechanism is activated causing a spark to ignite the released air fuel mixture in burner 29. When this occurs, the produced flame is positioned in flame tube assembly 13 (e.g. as shown in FIG. 6) located in the interior of upper housing component 4 when housing components 4 and 5 are connected together. The flame continues to stay lit until lever 2 is no longer depressed, whereby the control valve is closed, preventing the liquefied gas from evaporating and leaving fuel reservoir 17.

In other non-limiting embodiments, the igniter mechanism may instead include a piece of metal that is adjacent to a piece of flint whereby the metal strikes the flint creating a spark igniting the air fuel mixture to produce a flame from the burner that may be positioned near or in flame tube assembly 13. In a further embodiments, the vaporization device is an electronic heating mechanism including a power source, a circuit board, and a resistance wire similar to other vaporizers commonly used by those skilled in the art. The power supply is preferably a lithium battery but may be any type of power source, including those known in the art or yet to be developed, capable of transferring stored power to the circuit board. The lithium battery is connected to the circuit board and the circuit board is connected to the wire, whereby when the button connected to the circuit board is depressed, the wire powered by the lithium battery is heated enough to heat the flame tube assembly wires to a temperature that is capable of vaporizing the specific vaporizable substance. In further embodiments the temperature produced in the wire is adjustable by methods known by those of ordinary skill in the art.

A cartridge 6 is provided for containing vaporizable substance 7. Vaporizable substance 7 used may be any type of liquid, fluid, oil, or wax. Cartridge 6 may be filled with vaporizable substance 7 or, in other embodiments, cartridge 6 with vaporizable substance 7 may already be included. Located at the bottom of cartridge 6 is a plunger such as plunger 23 and a plunger grommet 22 such as plunger grommet 22, which are shown in the interior view provided in FIG. 6.

Cartridge 6 is able to fit into a compartment in upper housing component 4 with upper housing component 4 and cartridge in axial alignment and upper housing component 4 having a larger circumference than cartridge 6. When upper housing component 4 is connected to lower housing component 5, cartridge 6 aligns with a core such as core 24 (e.g. as shown in FIG. 6) located in lower housing component 5 and is enclosed within core 24. When upper housing component 4 and lower housing component 5 are attached, plunger 23 comes into contact with the straight rack 21. When button 1 is depressed, straight rack 21 moves axially in the upward direction and actuates plunger 23, pushing vaporizable substance 7 out of cartridge 6 into a compartment in a heating core top such as heating core top 11 as shown in FIG. 5, which is meant to illustrate an exploded view of various exemplary components that make up the upper housing component 4 of the exemplary vaporization device shown in FIGS. 1-8.

A pusher such as pusher 12 may be located in heating core top 11 enclosed in upper housing component 4 to move vaporizable substance 7 when pushed out of cartridge 6. Pusher 12 is preferably made of any type of metal, but this is non-limiting and pusher 12 may be made of any suitable material known in the art, such as, without limitation, higher durometer silicone or polytetrafluoroethylene. A second compression spring may be attached to the inside of upper housing component 4 and pusher 12. The second compression spring is provided to push back pusher 12 axially toward the left direction, away from the opening of cartridge 6 if the cartridge has been placed in the vaporization device, when button 1 is depressed.

In other non-limiting embodiments, a tension spring is attached to the inside of upper housing component 4 and pusher 12. The tension spring is provided for resiliently urging pusher 12 axially toward the left direction. When upper housing component 4 is connected to lower housing component 5, pusher 12 comes into contact with button 1 whereby pusher 12 is forced to the right of button 1 in the axial direction thus covering the outlet or opening of cartridge 6 if cartridge 6 has been placed in the vaporization device.

Figure 7:
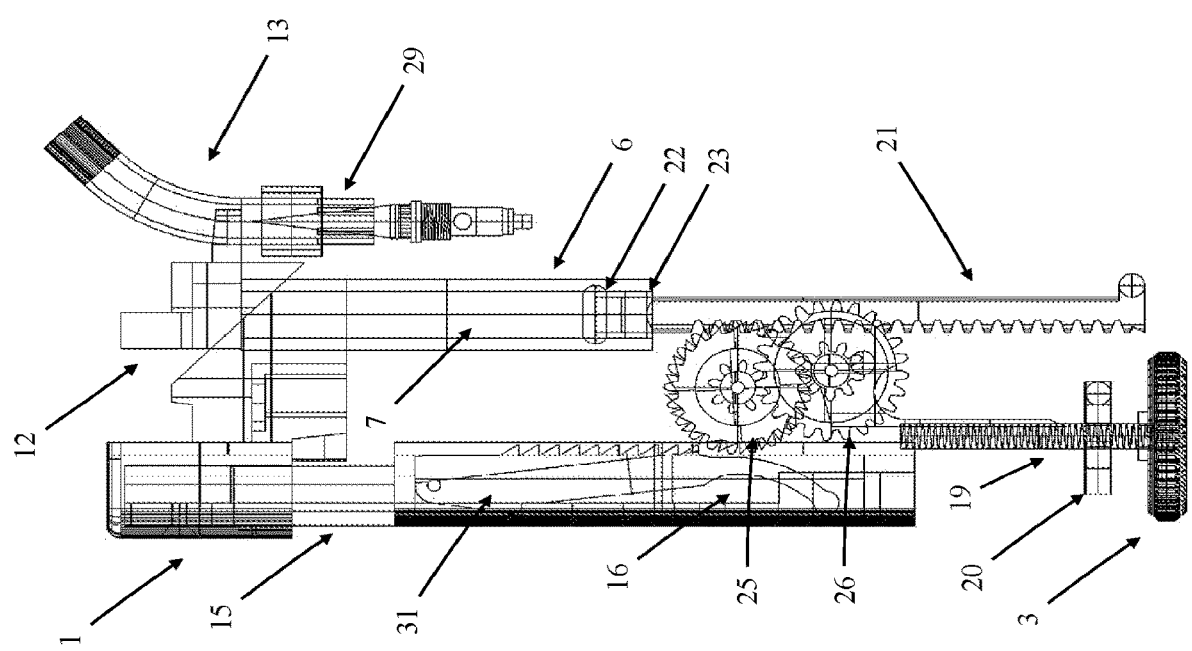
FIG. 7 shows a side view of the feeding mechanism in the disengaged position in accordance with an illustrative embodiment.
Figure 8:
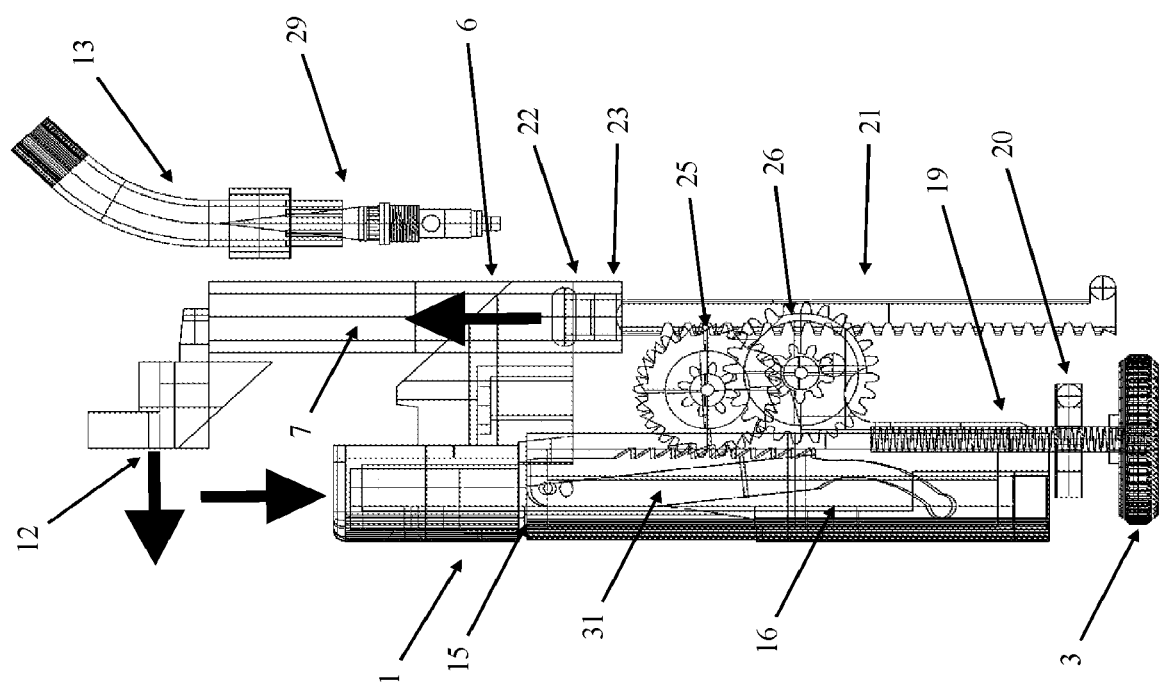
FIG. 8 shows a side view of the feeding mechanism in the engaged position in accordance with an illustrative embodiment.

When the button 1 is depressed, the first compression spring retracts and the pusher 12 moves left in the axial direction resting in this position, such as, for example as shown in FIG. 8. When button 1 is no longer depressed and the first compression spring moves button 1, button rack 16, and button bus 31 may move axially towards the upper direction overcoming the second compression spring's force and moving pusher 12 axially to the right direction covering outlet of cartridge 6 if cartridge 6 is placed in the vaporization device. When cartridge 6 is placed in the vaporization device and upper housing component 4 and lower housing component 5 are attached, pusher 12 will move axially toward the left direction when button 1 is depressed as vaporizable substance 7 is displaced out of cartridge 6 as shown in FIG. 7. When button 1 is no longer depressed button 1 moves back to its original position, forcing pusher 12 to move axially in the right direction moving vaporizable substance 7 that has been removed from the cartridge into heating core top 11 to come in contact with flame tube assembly 13 located inside of a heating core such as heating core 14 positioned inside of upper housing component 4.

Flame tube assembly 13 (e.g. as shown in FIG. 5) may include a flame tube and wire coils. In one embodiment, the flame tube may be a titanium tube with a 45-degree angle that is conductively heated from the flame inside of the flame tube. In other non-limiting embodiments, flame tube assembly 13 may be made of ceramic, borosilicate glass, quartz, stainless steel or any other material that is safe for consuming food at high temperature. In further non-limiting embodiments, the flame tube may be fixed at a different angle depending on the desired heat transfer and design. The flame tube can be described to have a heated end near burner 29 and an exhaust end where the burning gas exits. A titanium sheet such as titanium sheet 30 may be attached to lower housing component 5 around burner 29 to prevent unwanted gases from coming into heating core 14 surrounding flame tube assembly 13. Preferably stainless steel wire is wrapped around the flame tube.

There is also wiring inside the flame tube at the heated end, which serves to increase turbulence in the flame and conductively transfer extra heat into the walls of the flame tube. The wiring may be made out of other metals such as titanium. When vaporizable substance 7 comes into contact with flame tube assembly 13, vaporizable substance 7 may be moved in the middle of the flame tube between the heated end and the exhaust end where the flame tube is moderately hot. Vaporizable substance 7 becomes less viscous from the heat and trickles down the flame tube into a coil of wire wrapped around the heated end turning the vaporizable substance 7 into vapor.

In on embodiment, a mouthpiece such as mouthpiece 8 (e.g. as shown in FIG. 5) is connected to heating core 14 inside upper housing component 4 with a gasket such as gasket 9 arranged between mouthpiece 8 and heating core 14 to prevent leakage of the vapor. Gasket 9 is preferably made of silicone, but in other non-limiting embodiments, gasket 9 may be made of any material capable of sealing two mechanisms and is soft and suitable for food at high temperatures. Mouthpiece 8 is preferably made of titanium but may be made of ceramic, borosilicate glass, quartz, stainless steel or any other material that is safe for consuming food at high temperature.

In another embodiment, the exemplary vaporization device shown in FIGS. 1-8 may have an electronic temperature indicator coupled to a temperature sensor (not shown) such as those temperature sensors used by those of ordinary skilled in the art. In further embodiments, the temperature indicator could be analog. The temperature sensor should be located close to flame tube assembly 13 and heating core 14. In operation, the display will provide the user with an indication of the temperature. This is useful for some users who have difficultly using the vaporization device to achieve the most optimal vaporization temperature. The display may have an LED, or liquid crystal element to indicate an approximate temperature to the user, for example with a bar display screen. By monitoring the temperature on the display screen, the user can more accurately adjust the temperature inside heating core 14. In another embodiment the temperature sensor may be wired to a circuit board whereby when the temperature exceeds a certain degree, the circuit board closes the valve for releasing liquefied fuel from the fuel reservoir 17. In further embodiments the vaporization device will alert the user when the desired temperature is reached visually or audibly.

When vaporizable substance 7 is placed into cartridge 6, cartridge 6 is placed into upper housing component 4, upper housing component 4 is attached into lower housing component 5, and a setting on dosage dial 3 is selected, the vaporization device is ready for use. Lever 2 on the lower housing component 5 may be depressed by the user and the control valve is opened, evaporating the liquefied gas from fuel reservoir 17 where the gas is then supplied to burner 29 in flame tube assembly 13. Lever 2 also activates the piezoelectric ignition mechanism for causing the hammer to strike the quartz to cause a spark of electricity. The fuel line and wire carry the gas and electricity into flame tube assembly 13 where the gas is mixed with air and comes into contact with the spark of electricity, thereby producing a flame.

Once flame tube assembly 13 is heated, button 1 is then depressed by a user, causing straight rack 21 to actuate plunger 23 and plunger grommet 22 positioned in cartridge 6 causing an amount of vaporizable substance 7 to be moved out of cartridge 6 into heating core top 11 (shown in FIG. 5). Vaporizable substance 7 is then moved by pusher 12 into the middle of the flame tube in flame tube assembly 13 whereby vaporizable substance 7 becomes less viscous from the heat and trickles down the flame tube into a coil of wires wrapped around the heated end of the flame tube boiling vaporizable substance 7 into a vapor. To inhale vaporizable substance 7 once it has been heated, a user places mouthpiece 8 in to the user's mouth and breathes in, drawing air through the primary air inlet through heating core 14. The vapor created in heating core 14 is located in the air, thus the user inhales a mixture of air and vapor. Button 1 may be depressed repeatedly by the user and as many times the usher wishes and the vaporization device fire will remain lit until lever 2 is no longer depressed, closing the valve and stopping the flow of gas from fuel reservoir 17.

In an alternative embodiment, pusher 12 moves the vaporizable substance 7 into a reservoir positioned inside heating core 14 inside of upper housing component 4. The reservoir may be located above the flame on burner 29 that is created when lever 2 is depressed by the user whereby the flame transfers heat to the reservoir by conduction to heat the reservoir to a temperature capable of vaporizing the vaporizable substance.

Figure 9:
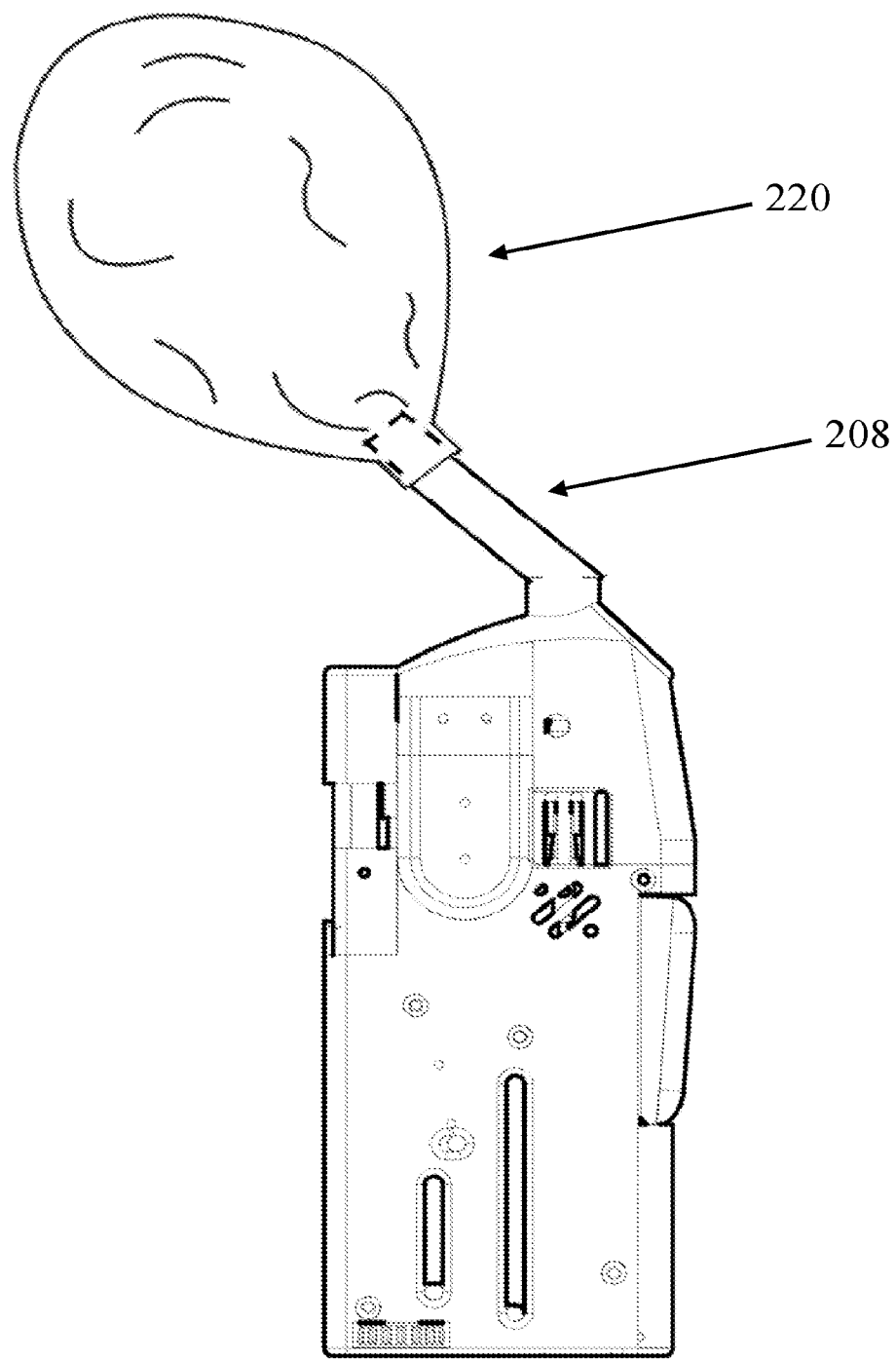
FIG. 9 shows a side view of the vaporization device with the inflatable pocket attachment.

In an alternate embodiment as shown in FIG. 9 the vaporization device includes an inflatable pocket attachment such as inflatable pocket 220 whereby the user may blow into an air inlet on the vaporization device, forcing the vapor out of an air outlet such as air outlet 208 on the vaporization device whereby inflatable pocket 220 may be detachably coupled at the exhausting end to out to air outlet 208 whereby the inflatable pocket 220 may collect and store vapor. Inflatable pocket 220 includes an inflatable pocket jacket, a retainer, and non-elastic heat resistant plastic, which can be darkly colored for the protection of the possibly light-sensitive contents. Inflatable pocket 220 may be removed from the vaporization device by detaching the neck from air outlet 208. When inflatable pocket 220 is detached from the vaporization device, inflatable pocket 220 is adapted for a user to inhale the vapor in inflatable pocket 220. In alternate embodiments, the vaporization device may be replaced with the attachment already built into the vaporization device or an attachment for the user to blow into. In further alternative embodiments, the vaporization device and attachments may be included along with the original functions of the other embodiments of the vaporization device.

This aforementioned description describes a vaporization device that may be used to heat vaporizable substances using a feeding mechanism to move the vaporizable substance from a cartridge and into a tube housing a flame activated by the user, turning the vaporizable substance less viscous, whereby then the vaporizable substance runs down the tube into a series of wires wrapped around the tube, vaporizable the vaporizable substance to be inhaled through a mouthpiece by the user. If the user wants to inhale a smaller amount of vapor, then the user can rotate the dosage dial on the vaporization device, restricting movement of the feeding mechanism to dispense a smaller dosage. If the user wants to a greater amount of vapor, then the user can set the dosage dial on the vaporization device to allow for a greater movement of the feeding mechanism to dispense a larger dosage of vaporizable substance from the cartridge and into the flame tube to be heated. The user may also dispense as many dosages as they wish by depressing the button multiple times, restarting the feeding mechanism.

The foregoing description of the invention has been presented for purposes of illustration and description and is not intended to be exhaustive or to limit the invention to the precise form disclosed. Many modifications and variations are possible in light of the above teaching. The embodiments were chosen and described to best explain the principles of the invention and its practical application to thereby enable others skilled in the art to best use the invention in various embodiments and with various modifications suited to the use contemplated. The scope of the invention is to be defined by the above claims.

What is claimed is:

1. A vaporization device for vaporizing substances, comprising:
   a housing having a storage compartment;
   a vaporizable substance stored within the storage compartment;
   a flame generator and a conductive-based heating surface configured to absorb heat from the flame generator;
   a feeding mechanism configpured to place the vaporizable substance from the storage compartment into contact with the conductive-based heating surface, the feeding mechanism comprising a component that is moved causing an amount of the vaporizable substance to be moved out of the storage compartment.

2. The vaporization device of claim 1, wherein the vaporizable substance is a liquid, fluid, oil, or wax.

3. The vaporization device of claim 1, the feeding mechanism further comprising an actuator, a physical mechanism, and a pusher, the actuator and the pusher are engageable, the actuator and the pusher having a first position when disengaged and a second position when engaged, the actuator coupled to the storage compartment wherein when the actuator is engaged an amount of the vaporizable substance is moved out of an opening of the storage compartment, the physical mechanism configured to be actuable on the pusher to apply force on the pusher, the pusher in the first position dimensioned to cover the opening of the storage compartment, the actuator in the first position configured to prevent force of the physical mechanism on the pusher, the actuator in the second position configured to no longer prevent force of the physical mechanism on the pusher, the pusher in the second position dimensioned to not cover the opening of the storage compartment.

4. The vaporization device of claim 3, wherein the physical mechanism is a compression spring and is connected to the housing.

5. The vaporization device of claim 3, the flame generator comprising a fuel tank, fuel stored within the fuel tank and an igniter.

6. The vaporization device of claim 5, wherein the fuel is a hydrocarbon held under pressure.

7. The vaporization device of claim 5, wherein the igniter is comprised of a piezo-electric crystal and a striking element.

8. The vaporization device of claim 5, wherein the igniter is engageable by the depressing of the actuator.

9. The vaporization device of claim 1, the feeding mechanism further comprising a dial, and a stop, the stop configured to physically limit the movement of the feeding mechanism when the dial is adjusted.

10. The vaporization device of claim 1, further comprising a mouthpiece, the mouthpiece having a first end and a second end wherein the first end is connected to the housing.

11. The vaporization device of claim 10, wherein the mouthpiece is detachable from the housing.

12. The vaporization device of claim 1, wherein the housing is formed of a first part and second part, the first part and second part configured to being fastened together to furnish an insulated housing around the flame generator, the second part housing the storage compartment and the flame generator, the first part connected to the mouthpiece.

13. A portable vaporization device for vaporizing substances, comprising:
    a housing having a storage compartment for holding a cartridge that is removable;
    vaporizable substance stored within the cartridge;
    a flame generator and a conductive-based heating surface configured to absorb heat from the flame generator;
    a feeding mechanism configured to place the vaporizable substance from the cartridge into contact with the conductive-based heating surface.

14. The portable vaporization device of claim 13, further comprising an air inlet having a first end and a second end, the first end connected to the housing, the second end connected to an inflatable pocket, the inflatable pocket configured to collect and store vapor, wherein the air outlet and air inlet are configured wherein when air is moved through the air inlet into the portable vaporization device, a vapor is forced through the outlet, filling the inflatable pocket wherein when detached from the second outlet the inflatable pocket is adapted for a user to inhale the vapor stored in the inflatable pocket or the second outlet.

15. A vaporization device for vaporizing substances, comprising:
    a housing having an upper component and a lower component the upper component removable from the lower component;
    a storage compartment within the lower component; wherein the storage compartment is configured to hold a cartridge wherein the cartridge is removable when the upper component and lower compartment are separated;
    a flame generator and a conductive-based heating surface configured to absorb heat from the flame generator; and
    a feeding mechanism configured to place the vaporizable substance from the cartridge into contact with the conductive-based heating surface.

16. The vaporization device of claim 15, the feeding mechanism comprising an actuator the actuator engageable, the actuator having a first position when disengaged and a second position when engaged, the actuator coupled to the storage compartment wherein when the actuator is engaged an amount of the vaporizable substance is moved out of the cartridge by a moving component.

17. The vaporization device of claim 16, the feeding mechanism further comprising a physical mechanism and a pusher, the pusher having a first position when disengaged and a second position when engaged, the physical mechanism configured to be actuable on the pusher to apply force on the pusher, the pusher in the first position dimensioned to cover the opening of the storage compartment, the actuator in the first position configured to prevent force of the physical mechanism on the pusher, wherein when the actuator in engaged the actuator no longer prevents force of the physical mechanism on the pusher, the pusher in the second position dimensioned to not cover the opening of the storage compartment.

18. The vaporization device of claim 17, the feeding mechanism further comprising a dial, the dial connected to a rod, the rod connected to a stop, the stop configured to physically prevent the movement of the feeding mechanism.

19. The vaporization device of claim 18, further comprising a mouthpiece, the mouthpiece having a first end and a second end wherein the first end connected to the housing by a gasket.

20. The vaporization device of claim 19, the flame generator comprising a fuel tank, fuel stored within the fuel tank, a venturi, and an igniter.

\* \* \* \* \*